United States Patent
Husher et al.

(10) Patent No.: US 11,402,396 B2
(45) Date of Patent: Aug. 2, 2022

(54) PROCESS RECORD SLIDE AND METHOD OF USING THE SAME FOR LOOSE CELLS

(71) Applicant: SHENZHEN PRS LIMITED, ShenZhen (CN)

(72) Inventors: Frederick K. Husher, Melbourne Beach, FL (US); Jee J. Shum, Miami, FL (US)

(73) Assignee: SHENZHEN PRS LIMITED, Shenzhen (CN)

( * ) Notice: Subject to any disclaimer, the term of this patent is extended or adjusted under 35 U.S.C. 154(b) by 0 days.

(21) Appl. No.: 17/137,911

(22) Filed: Dec. 30, 2020

(65) Prior Publication Data

US 2021/0199678 A1 Jul. 1, 2021

Related U.S. Application Data

(60) Provisional application No. 62/955,501, filed on Dec. 31, 2019.

(51) Int. Cl.
*G01N 1/30* (2006.01)
*G01N 35/00* (2006.01)

(52) U.S. Cl.
CPC ............ *G01N 35/00029* (2013.01); *G01N 2035/00138* (2013.01); *G01N 2035/00158* (2013.01); *G01N 2035/00168* (2013.01)

(58) Field of Classification Search
None
See application file for complete search history.

(56) References Cited

U.S. PATENT DOCUMENTS

2007/0141723 A1 6/2007 Sompuram et al.

FOREIGN PATENT DOCUMENTS

| WO | 2014165327 A1 | 10/2014 |
| WO | 2018228567 A1 | 12/2018 |

OTHER PUBLICATIONS

International Search Report and Written Opinion issued in corresponding International Application No. PCT/B2020/062554; dated Mar. 17, 2021; European Patent Office, 12 pgs.

*Primary Examiner* — Jyoti Nagpaul
(74) *Attorney, Agent, or Firm* — Hauptman Ham, LLP (57) ABSTRACT

The present application relates to process record slide and method of using the same for loose cells. A single to multi-region slide wherein each region contains one to four control targets and is suitable for processing through Special Stains, IHC or CC, and others. Each region may be bonded by a hydrophobic barrier to form a well. The slide has an adhesive coating suitable for capturing loose cells and cell debris.

20 Claims, 3 Drawing Sheets

PROCESS RECORD SLIDE AND METHOD OF USING THE SAME FOR LOOSE CELLS

PRIORITY CLAIM AND CROSS-REFERENCE

The instant application claims priority from U.S. Provisional Application No. 62/955,501, filed Dec. 31, 2019, the entirety of which is hereby incorporated herein by reference.

TECHNICAL FIELD

The present application relates to process record slide and method of using the same for loose cells.

BACKGROUND

There have been many versions of slides incorporating sample wells bounded by a hydrophobic barrier. Some of these slides have been developed and manufactured with many wells, for example 100 wells. However, none of these slides incorporates control targets to provide quantitative measure of the primary and secondary stain reagents used to process the samples.

A method by which antibody reagent concentration is determined involves determining the absorbance of a diluted sample at 280 nm. The assay report is then generated to give the concentration of the packaged vial, usually between 0.8 to 1.2 mg/ml. However, the absorbance measurement assumes that all the antibody proteins are fully intact. If hinge is broken at some percentage, but both the Fab and Fc domains are still present, the measurement remains the same. As the antibody is used, the temperature of the antibody is increased to 25° C. before aliquots are withdrawn. When further processing of slides is no longer desired, the vial is returned to storage at 4° C. All proteins will break down with age, starting with failure at the hinge. To address this decay in viable antibodies, a lab protocol is simply to discard the vial after 6-month has passed since purchase. The presumption is the degradation is not serious enough to affect the stained tissue section. However, leaving the vial out overnight would significantly shorten the lifetime of the antibody viability. Because of the antibody expense, most of the time labs just ignore this defect, and hope to obtain the best result. Only when using a known cellular control, such an early failure would become visible.

SUMMARY

A slide of some embodiments of the present application addresses this situation through the inclusion of control targets within each sample well. A function of the control targets is to quantify the functional concentration of the applied primary antibody.

There is no co-resident process quality controls (PQC) solutions for loose cell-based slides. Loose cell applications include Pap Smears, blood smears, and the multi-well/multi-patient slides being used in various applications. Most commonly, the multi-patient slides are used for volume processing of Pap smears, Capturing the loose cells from the applied slurry occurs by giving the deposit enough time for the cells to sink to the slide surface. The slide incorporates an adhesive coating that covalently captures the cells when the cells settle down. In some embodiment, a conformal adhesive is used over a mono-layer adhesive to ensure a higher binding density between the cell and the adhesive. An example of such a conformal adhesive slide is the Erie Gold Plus. Although in some instances, a good quality amino-silane slide adhesive will be sufficient in capture performance.

Slides with sample wells can be fabricated by printing a pattern using a hydrophobic paint, such as epoxy or urethane. Several printing processes are usable and can include screen printing, pad printing, inkjet, or roller ball. Such slides are fabricated by a number of vendors. A factor in the printing process is no heat is applied to cure the paint, as the heat will usually reduce the hydrophilic behavior of the adhesive.

In some applications, the use of a hydrophobic barrier is not viable. An example is a blood smear, where the smear process tends to separate the blood cell types in the specific regions of the smear. The smear is usually formed by drawing or pulling the sample drop by the back-side of the wedge. The speed and wedge angle is a function of the blood's viscosity. PQC targets can be placed as fiducial marks on the slide to inform the user where the patient sample should be applied.

Single sample slides may or may not utilize a hydrophobic barrier. In classic form, both blood and Pap smear slides can be made without any hydrophobic barrier ring. Automated Pap smear machines process the patient sample into a controlled cell density slurry or as a wet layer on a filter disk. The slurry is applied within a hydrophobic barrier ring to settle down over a period of time, whence the excess liquid is removed. An example of which is unreleased Veracell Pap smear slide. The wet layer on a filter disk is transfer printed onto a slide and thus does not need a retainment barrier ring. An example of which is the ThinPrep slide.

Some embodiments of the present application herein incorporate PRS control targets as fiducial marks for slides without hydrophobic barriers. As fiducial marks, the control target dots will be located in the four corners of the working area, nominally defined as a region of 1.5 cm×1.5 cm. As a general rule, slides not using hydrophobic barriers will handle only one patient sample of biomaterial. Control targets would be located along the edges within the 1.5 cm×1.5 cm region. While FIG. 1A includes a 1.5 cm×1.5 cm region, one of ordinary skill in the art would understand that different size regions are within the scope of this disclosure.

Slides incorporating hydrophobic barrier rings for sample containment rarely exceed 10 wells, each well comprising a containment area. The sample is applied at the center of the well and the well filled to nearly the spillover volume. Cells tend to drop out away from the well's edge and can pile up at the center as the carrier buffer evaporates, especially if accelerated by the application of heat. The control targets would be spaced into four equidistant sites at the working periphery of the well. The staining reagents: antibody proteins for IHC applications precipitate faster than cells tending to have their highest concentration at the edge of the deposit. Thus, the cell slurry will generally avoid settling where the targets are. The stain reagents however, will have sufficient time to be captured by the control targets. As with any staining process, once the biomaterials are wet, the biomaterials normally remain wet until the staining has been completed.

The staining process is limited to supporting two primary antibodies, with the proviso that one antibody be mouse based and the other antibody is rabbit hosted. In a single primary antibody configuration, the control target will capture either mouse or rabbit hosted antibodies. There are a number of configuration options that can be applied to the control targets:

A 4-dot gradient density series for a single primary antibody (either mouse or rabbit based);

A 2-dot gradient density series with one pair for the mouse antibody and the other pair for the rabbit antibody;

4 target dots which can be a mouse antibody, rabbit antibody, mouse secondary antibody, and mouse secondary antibody; or Any combination of the above.

Some embodiments of the present application are directed to a slide comprising a detection area configured to hold a sample comprising loose cells, and a control area configured to:

indicate an error and performance measure of intermediate steps during an immunohistochemical or an cytochemical detection process, and provide a reference for qualitatively or quantitatively determining the antigen density and color density of the stained loose cells or color density on and within the stained cells respectively, wherein the detection area comprises at least one region, the control area is around the at least one region of the detection area, and the control area comprises at least one control target for providing the reference.

In at least one embodiment, further comprises an adhesive coating configured to bind with moieties, wherein the adhesive coating comprises at least one end group selected from the group consisting of —ROH, —R(C=O)OH, —RNH$_2$, —R(C=O)NH$_2$, and —RNH$_3$.

In at least one embodiment, each of the at least one well of the detection area is a round, a square or a rectangle.

In at least one embodiment, the control area is at a corner of the region of the detection area.

In at least one embodiment, the control area is inside the region of the detection area.

In at least one embodiment, the control area is outside the region of the detection area.

In at least one embodiment, the control area comprises at least one control dot or an array of control dots.

In at least one embodiment, the control target is composed to capture mouse, rabbit, or mouse+rabbit hosted primary antibody; mouse, rabbit, or mouse+rabbit secondary antibody; or hematoxylin and eosin stains.

In at least one embodiment, the primary antibody is captured at its FcyRI site by either Protein A, Protein G, Protein A/G, or a FcyRI binding peptide attached to a carrier protein or bead including a material such as Latex.

In at least one embodiment, the hematoxylin and eosin are captured by a chemical target attached to an amine coated bead including a material such as Latex.

In at least one embodiment, a pair of the primary target comprises two different concentrations, one at 100% and the other between 30 and 70%.

In at least one embodiment, further comprising a layer of adhesive.

In at least one embodiment, the adhesive is amino-silane.

In at least one embodiment, the control area is bounded by a partial or complete hydrophobic barrier.

In at least one embodiment, the at least one well of the detection area comprises the sample.

In at least one embodiment, further comprising a hydrophobic material coating.

In at least one embodiment, the hydrophobic material is epoxy or urethane.

In at least one embodiment, the control target comprises a primary target, a primary antibody, a secondary target, a secondary antibody, an imaging reference, a 2D imaging reference target, a 3D imaging reference target, or a target array.

In at least one embodiment, secondary targets can be of two different concentrations, one at 100% and the between 30 and 70%.

In at least one embodiment, the reference imaging dot comprises at least one:

A black reference target comprising carbon dust;

A white reference target, wherein the white reference target comprises a metal oxide or a metal sulfate; or A clear target, wherein the clear target comprises a non-reactive protein to any immunohistochemical, immunochemical, or cytochemical reagents.

In at least one embodiment, the imaging reference dot comprises an anhydride-based epoxy for a white reference target and a black reference target; and A protein from the equine family of mammals for a clear target.

Some embodiments of the present application also are directed to a method of using the above slide for detecting cells, the method comprising:

placing the sample comprising loose cells in the detection area, placing a control target in the control area, staining the loose cells and the control target, wherein the staining process comprises:

applying at least one primary target to the control area of the slide, applying at least one primary target conjugated with the moiety to the control area of the slide, or applying at least one secondary target conjugated with a moiety to the control area of the slide, and applying a stain reagent producing color to the detection area and the control area, assessing a quality of the staining process, wherein the assessing process comprises assessing the staining result of the loose cells and the control target, qualitative determining the status of the loose cells.

In at least one embodiment, the at least one control target is configured to capture mouse, rabbit, or mouse+rabbit hosted primary antibody; mouse, rabbit, or mouse+rabbit secondary antibody; or hematoxylin and eosin stains.

In at least one embodiment, the primary antibody is captured at a FcyRI site by either Protein A, Protein G, Protein A/G, or a FcyRI binding peptide attached to a carrier protein or activated bead.

In at least one embodiment, the hematoxylin and eosin are captured by a chemical target attached to an activated bead.

DETAILED DESCRIPTION

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

In addition, reagents used in immunohistochemical methods as well as immunochemical methods, such as enzyme solutions and peroxidase color development reagents, have limited stability at working temperature or at room temperature. The limited stability results in frequent preparation of the reagents. Furthermore, nonspecific antibody binding which leads to erroneous results remains a problem.

Primary Targets

In some embodiments, the control targets 102 include one or more primary targets to test primary antibody reagents.

As used herein, the term "primary targets" means a composition of reactive and non-reactive elements that specifically bind to a primary antibody by only one of its FcyR1 sites. As used herein, the term "primary protein" means a protein that binds to the FcyRI of the primary antibody. As used herein, the term "primary dummy protein" means a protein that will not react to any primary antibody or secondary antibodies. As used herein, the term "maximum target density" refers to the maximum monolayer density of adjacent proteins. As used herein, the term "surrogate antigen" refers to a protein that is not targeted by the primary antibody used in the IHC or the ICC assay, but nonetheless binds to the primary antibody via, for example, only one of the two FcyRI regions of the primary antibody (mouse or rabbit based) used in the IHC or the ICC assay. As used herein, the term "mouse only surrogate antigen" means a protein or antigen that uniquely reacts to only to the FcyRI of mouse based primary antibody. As used herein, the term "rabbit only surrogate antigen" means a peptide or protein that uniquely reacts to only the FcyR1 of a rabbit based primary antibody.

Placenta mammal proteins range between 50-65 kDa in weight. Primary antibody IgG proteins are composed of two Fab and one Fc domains that are usually modeled with a Y-shape. The Fc is joined to the two Fab domains by a hinge. All non-conjugated antibodies are grown within a host mammal (most often Mouse or Rabbit) through inoculation of the host by an antagonist antigen peptide. The host produces antibodies to fight off the offending antagonist antigen peptide by assembling a binding amino acid sequence near the N-terminal end of the antibody's Fab domain that can capture the mating antigen. The Fc domain of the antibody is always that of the host mammal. The Fc domain of the host antibody typically has three binding sites available to the secondary antibody in rank order of highest binding affinity to lowest: FcyRI (CD64), FcyRII (CD32), and FcyRIII (CD16).

The primary dummy protein is chosen to be unreactive to mouse, rabbit, goat, bovine, and sheep as these can often bind to the secondary antibody. In some embodiments, the dummy primary protein is any member of the Equine family: horse, donkey, zebra, taper, or rhino. BSA (bovine serum albumin) is not a suitable dummy protein as BSA will not bind covalently to the tissue or most slide adhesive chemistries without heat and time. Bovine, sheep, and goat are also not suitable dummy proteins as in some cases these proteins may be confused with mouse or rabbit depending on the specificity of the primary antibody.

The primary protein is either host anti-mouse or host anti-rabbit. The host is limited to goat or any member of the equine family.

Primary proteins based on peptides can also be composed of mouse or rabbit FcyRI reactive peptides with cysteine residues at the C-terminal end covalently attached to a carrier protein such as KLH subunit (keyhole limpet hemocyanin). The KLH subunit is activated with Sulfo-SMCC at its free amine sites, which through conjugation binds to the cysteine residue of the peptide. Un-activated KLH subunit alone suffices to make the primary dummy protein.

KLH as a full protein is approximately 8000 kDa. In the full protein state, KLH is not stable in regards to pH or temperature, which will cause the protein to separate into subunits: KLH1 at 390 kDa and KLH2 @350 kDa. Either of these subunits can be used as carrier proteins, when Sulfo-SMCC activated, for peptides with a cysteine residue, usually at the C-terminal end of the peptide.

Figure 1A:
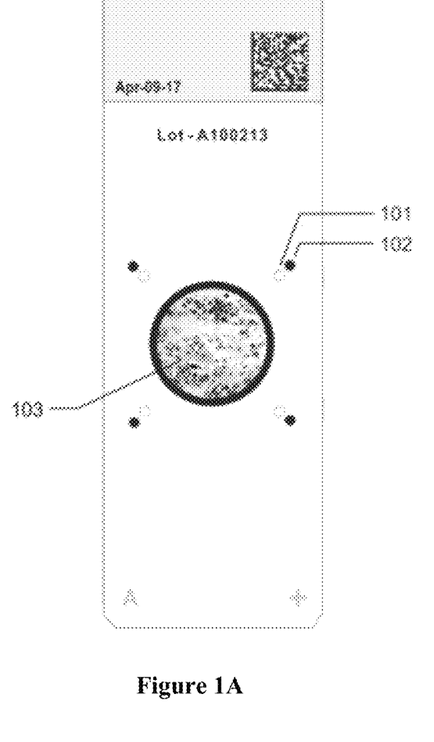
FIG. 1A is a top view of a slide with a hydrophobic barrier ring that also contains control targets in accordance with at least one embodiment.
Figure 1B:
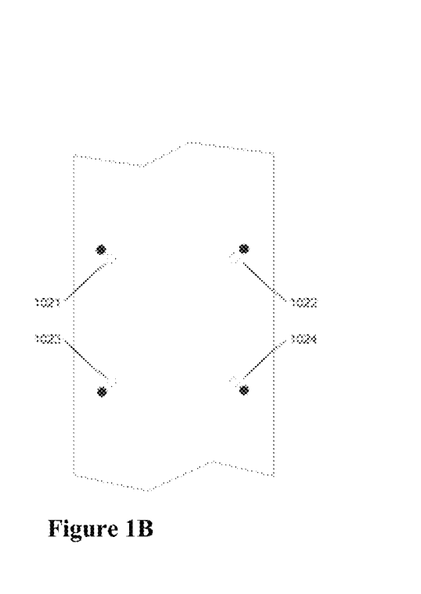
FIG. 1B is a top view of a portion of a slide with a hydrophobic barrier ring that also contains control targets in accordance with at least one embodiment.
Figure 2:
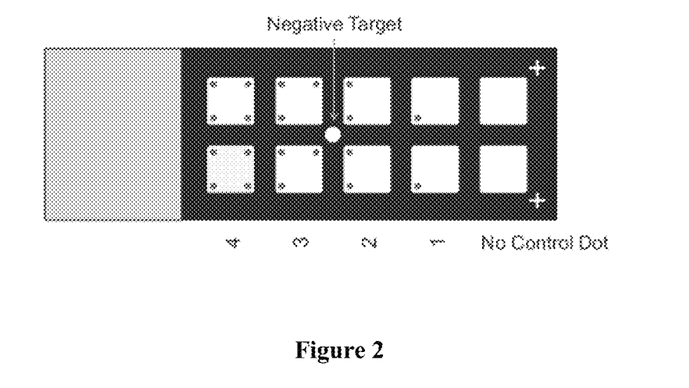
FIG. 2 is a top view of a slide with hydrophobic barrier rings that each contains control targets in accordance with at least one embodiment.
Figure 3A:
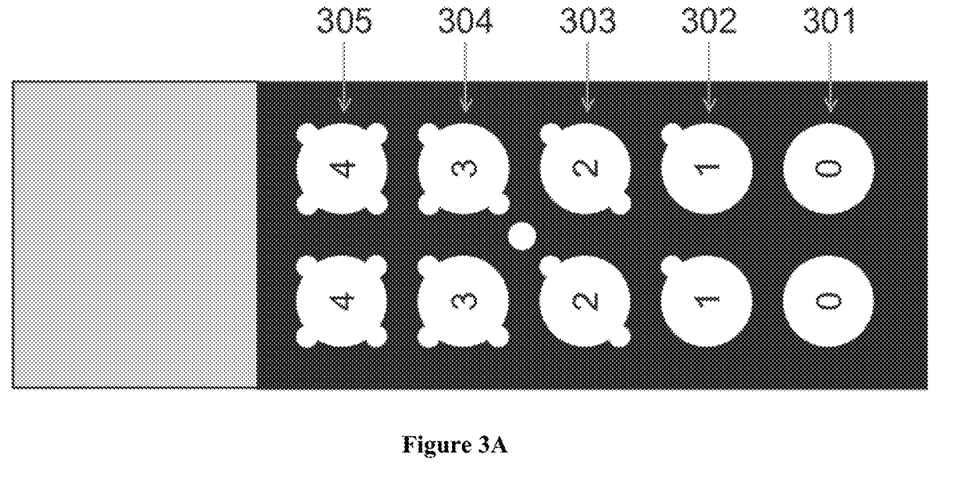
FIG. 3A is a top view of a Pap test slide that has control targets for the p16INK4a and Ki-67 primary antibodies in accordance with at least one embodiment.
Figure 3B:
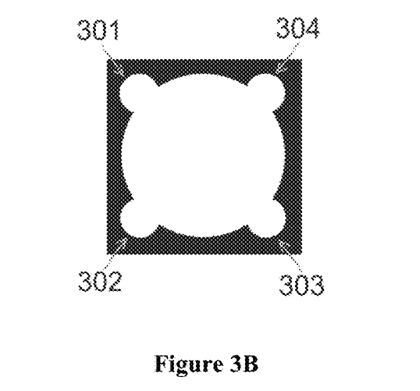
FIG. 3B is a top view of a control target for the p16INK4a and Ki-67 primary antibodies in accordance with at least one embodiment.

Refer to FIG. 1, in some embodiments, the primary targets are arranged into a primary target array 1021 through 1024. In some embodiments, the primary target array 102 is a primary target density gradient array. In some embodiments, each target within the array has the same maximum target density (proteins/surface area). However, the ratio between primary and dummy primary proteins are stepped in ratio to ensure that a wide range of primary antibody dilutions can be identified. As a general rule, detection by two primary surrogate antigen targets is sufficient to map the concentration to the detection transfer curve. In some embodiments, the primary target density gradient array includes a plurality of primary target loading dots wherein one array is mouse based and the other rabbit based.

In some embodiments, the density of the primary targets increases or decreases in a linear manner, such as 100%, 80%, 60%, 40%, etc. In some embodiments, the density of the primary targets increases or decreases in a logarithm manner, such as 100%, 33%, 10%, 3%, etc.

In some embodiments, in a primary target density gradient array, in the loading dot having the highest primary target density, the primary target density is sufficiently high so that the primary target is not able to saturate the loading dot during the staining process.

In some embodiments, the universal surrogate antigen is either Protein A or Protein G. Protein A binds to the FcyRI and to some areas within the Fab domain of placenta mammals. Protein G will bind only to the FcyRI site of most placenta mammals.

In some embodiments, the surrogate antigen has specificity to mouse or rabbit only. To support the specificity, the surrogate antigen can be composed of anti-mouse and anti-rabbit proteins, anti-mouse and anti-rabbit peptides on a carrier protein, or anti-mouse and anti-rabbit VHH protein domains all respectively.

In some embodiments, the dummy surrogate antigen includes an antibody from an animal of the equine family or a hoofed placenta mammal except goat. Equine family includes animals such as horses, donkeys, tapirs, rhinos and mules. The equine family are evolutionarily and genetically further apart thus reducing the occurrence of non-specific staining. Goat cannot be used as often the secondary stain uses an anti-goat protein in its sequencing, which would bind to any unreacted goat primary sites.

Although the manner of interaction between the surrogate antigen and the primary antibody used in the staining process is different from those between the actual antigen and the primary antibody, the surrogate antigen targets can provide a valuation of the primary antibody's efficacy. The primary antibody comes with an assay of the concentration in mg/ml. However, the assay does not indicate what percentage of the assay represents complete IgG proteins. Since the density concentrations of the surrogate antigen in the targets are known the capture of the applied primary antibody concentration can be determined. By extrapolation the antigen density of the co-resident tissue section can be determined. The resolvability of antigen density on the tissue is limited to the cumulative displacement by the primary antibody (monoclonal or polyclonal), secondary antibody and enzyme gain of the secondary stain. The concentration of the applied primary antibody is dependent upon the tissue type and always has some excess margin included. Thus, the assumption is that the primary antibody will bind to all the available antigen sites within its displacement limitations.

In some embodiments, the primary target density gradient array is a loading dot array of a universal surrogate antigen. In some embodiments, the loading dots in the array includes increasing or decreasing density of the surrogate antigen. In some embodiments, the surrogate antigen is blended with one or more dummy proteins, such as dummy surrogate antibodies, and the increasing or decreasing concentration of the surrogate antigen is achieved by altering the ratio between the surrogate antigen and the dummy protein while maintaining the maximum target density.

In some embodiments, the control area 102 includes at least two arrays of surrogate antigen target. In some embodiments, the control area 140 includes a first surrogate antigen target array including an anti-mouse antibody and a second surrogate antigen target array including an anti-rabbit antibody, both blended with a dummy surrogate antigen to form the desired reactive density while maintaining the maximum target density.

Therefore, according to these embodiments, with the IHC or ICC steps the surrogate antigen primary targets can evaluate the primary antibody concentration using the enzyme gain and antigen retrieval factors developed by the secondary targets.

2D/3D Targets

In some embodiments, the control targets, such as the primary target, the secondary target or the antigen retrieval targets include a 2D target.

As used herein, the term "2D target" means that the peptide, protein, antigen, antibody or any other control target materials are deposited on a 2D plane on the slide.

2D targets are easier to deposit and are therefore relatively cheap to manufacture. Therefore, 2D targets are preferred when cost is concerned.

In some embodiments, the control targets, such as the primary target, the second target or the antigen retrieval targets include a 3D target.

As used herein, the term "3D target" means that at least one of the peptide, protein, antigen, antibody or any other control target materials are applied to a support structure and the composite deposited in a 3D space on the slide.

In one or more embodiments, 3D targets are constructed by forming a 3D scaffold on the slide, and depositing the control target materials on the scaffold. In some embodiments, the 3D scaffold is a polysaccharide cluster. The polysaccharides form covalent bonds with the hydroxyl or amine groups on peptides or on the surface of the protein, which links proteins together and anchors the target to the slide coating adhesive. In some embodiments, the control targets are fixed on the 3D scaffold by formaldehyde fixation. The target is then composed of both 2D and 3D components.

In one or more embodiments, the 3D targets are constructed from submicron beads to which the primary or secondary target materials are covalently bound. Formaldehyde fixation is then applied to stabilize the primary or secondary target materials against normal antigen retrieval processing. The deposited target then consists of 2D and 3D components.

Comparing to 2D targets, 3D targets behaves more similar to the staining samples. Staining samples of IHC or ICC, such as tissue sections and cells, have heights. The height of the samples commonly ranges from 4 microns to 10 microns. Antigen sites targeted in the staining can be anywhere on the exposed surface topology of the tissue section. As such, antigen sites in the sample can be planar at either top of bottom surface of the section or anywhere along a sidewall of the tissue. Thus, the antigen on the sidewall of the sample is able to precipitate significantly more colorant from the chromogen than the 2D targets are able to. The inclusion of the 3D elements with the 2D elements creates a step offset that can be applied to the other 2D target dots to form a virtual 3D array. Experimentally, the inventors found that any 3D target between 80 nm and 0.5 um would stain as darkly as the tissue section. Beads of larger than 0.6 um cause too much loss optical loss with transmitted light illumination, making the beads appear dark even with no staining taking place. This is however, not an issue when reflected light illumination is used.

In addition, DAB, a reagent commonly used in the staining process, ages over a relatively short amount of time resulting the changes of color and intensity. The instant inventors have found that in the DAB stained 3D targets the color and intensity changes in a manner similar to those in the sample.

Special Stains

In some embodiments, the control targets include a special stain.

In some embodiments, the special stain includes Alcian Blue, Analine Blue-Orange G Solution, Azan Stain, Bielschowsky silver stain, Brow & Benn-Gramm Stain, Cresyl Violet, DAB, Fontana Masson, Gordon and Sweet's silver staining, Grocett's Methanamine silver method, Hall's Bilirubin stain, Jones Methanamine silver method, Luxol Fast Blue, Luxol Fast Blue-Cresyl Violet, Mucicarmine (Mayer's Method), Muller-Mowry colloidal Iron, Orange G, Nuclear Fast Red, PAS with Diastase Digestion, Periodic Acid Schiff (PAS), Phosphotungstic Acid, Haematoxylin, Picro Sirius Red, Toluidine Blue Acidified, Trichrome-Gomoris One-Step, Trichrome-Masson's, Victoria Blue, Von Kossa, Weigert's Resorcin Fuchsin, Weigert's Iron Haematoxylin, Zell-Neelsen Method, or combinations thereof.

Submicron latex beads are available in sizes ranging from 200 nm to 5 um in diameter—with exposed amine sites on their surface. As described in WO2018/228576, the chemical targets all have hydroxyl end groups to be used to bind with the amines on the latex bead. The reaction rate is slow, but with steady rocking the reaction can be completed in 24 hrs.

Imaging Reference Target

In some embodiments, the control area 102 further includes an imagining reference target. In some embodiments, the image reference target includes a black target or targets, a white target or targets, or a clear target.

Digital imaging of microscope slides containing stained biomaterials is evolving to perform prescreening and potentially full diagnostic determination on the stained materials. In some embodiments, after the staining process, the slide is subject to an imaging process during which the light illumination level or exposure are adjusted so that the digital image is not in compression at either the white or black boundary. The underlying assumption is that the white and black targets represent the extremes that the level of staining signals can reach. However, in doing so there is compression in the digital scale as the black is much blacker and the white much whiter than can realized by the staining of a tissue section.

In some embodiments, there are two imaging reference control targets located exterior or within the hydrophobic barrier, but not within the sample wells, that represent the black and white references for transmitted and reflective light imaging.

| Imaging Reference | Transmitted Light | Reflected Light |
|---|---|---|
| White | Clear dot | Black pigment dot |
| Black | Black pigment dot | Clear dot |

As the epoxy paint is inherently shiny the epoxy paint has a high $1^{st}$ surface reflection that appears to be the white reference by the ocular for reflective light illumination. With transmitted light the same black dot obscures the light transmission to become the transmitted black reference. The clear dot functions as the white reference for transmitted light while appearing as the black reference for reflected light. To simplify the fabrication of the hydrophobic barrier fabrication, the barrier material is a black epoxy paint which has an additional small well that becomes the other imaging reference as described earlier.

Imaging with transmitted light results in a misrepresentation of the antigen density on the tissue. This occurs because the stained tissue is not a monolithic slab where all antigen sites are on a single plane. Rather, the tissue can have antigen sites anywhere within its thickness. The secondary stain produces colorant particles that continue to precipitate until the particles cover the enzyme site and block continued precipitation. Should an antigen site be on the sidewall of the tissue section, the enzyme will never become covered and the precipitation will over express the antigen presence. With transmitted light the 'darkness' occurs because the precipitated colorant is thicker. In contrast, reflected light only 'sees' the top surface of the colorant pile resulting in a more accurate representation of antigen density.

In some embodiments, the white target has a color close to perfect white. Because a perfect white color is difficult to obtain, in some embodiments, the color of the white target is 5-10% away from perfect white. White colors less than 5% away from perfect white is difficult to produce, and colors more than 10% away from perfect white are sometimes not accurate enough as a control for staining signal strength.

In some embodiments, the white target includes a white pigment. In some embodiments, the white pigment is a metal oxide or a metal sulfate pigment that is stable with the passage of time when not left exposed to strong light. In some embodiments, the white pigment includes aluminum oxide, titanium oxide, or barium sulfate. In some embodiments, the metal oxide or the metal sulfate is in the form of beads.

In some embodiments, the black target includes a black pigment. In some embodiments, the black pigment includes a carbon-based pigment. In some embodiments, the black pigment includes a carbon dust. In some embodiments, a diameter of the carbon dust is less than 2 microns.

In some embodiments, the imaging reference target formulation is free of a surfactant, thereby preventing the ink/paint to be reactive to the range of stains and reagents these slides can experience.

In some embodiments, the imaging reference target is printed on the slide by a pad stamp. In other embodiments, the imaging reference target is printed by a syringe, because the syringe is able to control a size of target deposition.

Using the imaging reference targets, digital analysis is optimized because the all of the digitization range is within the slide's definition of black/white versus the use of perfect black and white references. The digital analysis assists with interpolation of a color of the control targets in order to more precisely determine an amount of antigen present in the stained sample. The image reference target is used in order to assist with calibration of the digital analysis in order to provide a reference point for measuring an amount of reaction at the control targets.

Method of Depositing Control Targets

In some embodiments, the instant specification is directed to a method of depositing control targets on a process recording slide. In some embodiments, the slide and the control targets are the same as or similar to those as described above.

In some embodiments, the method of depositing control targets including depositing a primary control target or a secondary control target on the slide.

In some embodiments, depositing the primary control target or the secondary control target includes: preparing a solution of the control target at a predetermined concentration; fixing the control target; and printing the solution onto the slide.

In some embodiments, preparing the solution of the control target includes preparing a solution including the control target and a polysaccharide to function as the linker between the proteins and the slide adhesive.

In some embodiments, fixing the control target includes fixing the control target with formaldehyde. The formaldehyde crosslinks the control targets so that the control targets can withstand normal antigen retrieval protocols.

In some embodiments, the control targets are crosslinked. Within tissue, proteins are bound to other parts of the tissue that tend to keep the proteins from diffusion and denaturation. Since the control targets in the solution includes loose proteins, the control targets are more sensitive to heat and pH and, as such, tend to diffuse and denature on the slide, especially when going through the AR process in IHC or ICC.

Fungal growth inhibitor can be Thimerosal or a green alternative of pridine-2-sulfinate sodium salt (Krovin 500).

In some embodiments, the primary targets are prepared as follows:

Form a set of the primary protein master dilutions of 1 ml with a concentration of 45 μg/ml. Dilute the Donkey-anti-Mouse, Donkey-anti-Rabbit, and Donkey IgG (H&L) proteins with dH2O as needed to realize the 45 μg/ml concentration. Typically, these proteins are between 1 and 10 mg/ml in concentration as purchased. Add in 10 μl of a fungal growth inhibitor. Fungal growth inhibitor can be Thimerosal or a green alternative of pridine-2-sulfinate sodium salt (Krovin 500).

Fix each master dilution with 10 μl 0.2% formaldehyde for 1-4 hrs at 40-60° C.

Add in 30 μl of 0.45% concentration amylose as a linear polymer (including a fungal growth inhibitor) and mix for 30-min Add in 20 μl of 0.1M ammonium bicarbonate to quench any unreacted formaldehyde Use the master protein solutions to form the target mixtures of Mouse with Donkey and Rabbit with Donkey, wherein each target contains 700 μl of the master protein solutions.

In some embodiments, the secondary targets are prepared as follows:

Form a set of the secondary protein master dilutions of 1 ml with a concentration of 45 μg/ml. Dilute the Mouse, Rabbit, and Donkey IgG (H&L) proteins with $dH_2O$ as needed to realize the 45 μg/ml concentration. Typically, these proteins are between 10 and 60 mg/ml in concentration as purchased. Add in 10 μl of a fungal growth inhibitor.

Fix each master dilution with 10 μl 0.2% formaldehyde for 1-4 hrs at 40-50° C.

Add in 30 μl of 0.45% concentration amylose as a linear polymer (has a fungal growth inhibitor) and mix for 30-min Add in 20 μl of 0.1M ammonium bicarbonate to quench any unreacted formaldehyde Use the master protein solutions to form the target mixtures of Mouse with Donkey and Rabbit with Donkey, wherein each target contains 700 μl of the master protein solutions.

In some embodiments, the prepared primary or secondary targets, or image reference targets are printed onto the slide in one print cycle according to the follows:

Print the target solutions onto an adhesive coated microscope

Air dry at 60° C. until all water has been evaporated then cool

Apply the paraffin-solvent mixture by spray over the printed target arrays

Reflow the paraffin to complete sealing of the targets arrays and drive off the solvent. Thus, returning the paraffin into its hardened and solid state.

EXAMPLES

The following examples are intended to illustrate, but not limit the disclosure. While the following examples are types of examples are typical of those that might be used, other procedures known to those skilled in the art may alternatively be used.

The materials used in the Examples are available from commercial purchase.

Example 1. P16INK4a & Ki-67 Sample Slide with Integrated Process Quality Control Currently there are multi-well test slides that support P16INK4a and Ki-67 staining, but these multi-well test slides lack any controls so stained results assume that the AR processing was done in compliance with the protocol and that the primary antibody reagents are consistent as to their functioning with consistent efficacy between slides or between lot codes of the antibodies.

Figure 4:
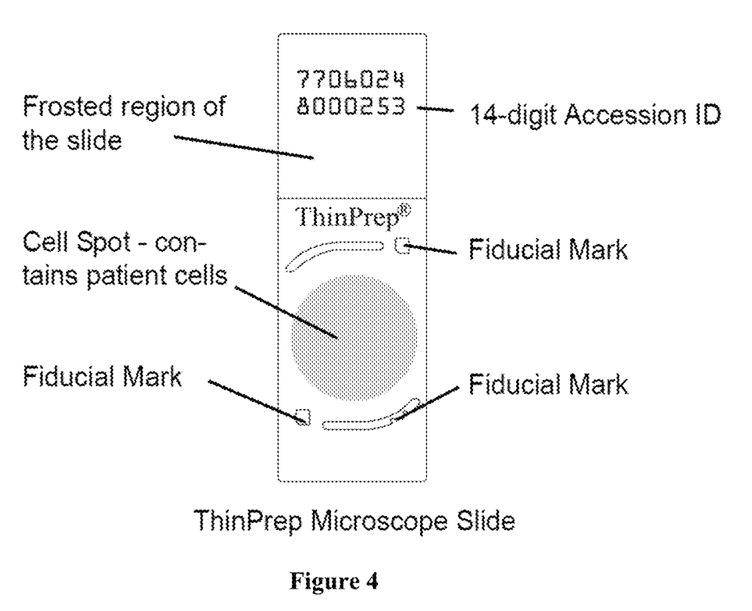
FIG. 4 is a top view of a ThinPrep compatible Pap smear slide for supporting PQC targets for Pap staining in accordance with at least one embodiment.

FIG. 4 illustrates an example of a 10-well, wherein each well contains four control targets. The four control targets are split into pairs for each primary antibody, one with a mouse host and the other a rabbit host. The pair consists of a 100% 2D/3D target and a 50% 2D/3D target. The targets function to verify that the primary antibodies were applied and that their concentration was sufficient to stain the cells, containing the matching antigen sites, within the well correctly.

Additionally, there are two imaging reference control targets located exterior or within the hydrophobic barrier, but not within the sample wells, that represent the black and white references for transmitted and reflective light imaging.

| Imaging Reference | Transmitted Light | Reflected Light |
|---|---|---|
| White | Clear dot | Black pigment dot |
| Black | Black pigment dot | Clear dot |

As the epoxy paint is inherently shiny the epoxy paint has a high $1^{st}$ surface reflection that appears to be the white reference by the ocular for reflective light illumination. With transmitted light the same black dot obscures the light transmission to become the transmitted black reference. The clear dot functions as the white reference for transmitted light while appearing as the black reference for reflected light. To simplify the fabrication of the hydrophobic barrier fabrication, the barrier material is a black epoxy paint which has an additional small well that becomes the other imaging reference as described earlier.

The targets are located around the patient sample area is that labs sought to minimize the amount of reagents used and often did not use enough method to process the sample correctly. By having targets at the four corners, confirming that sufficient stain materials have been applied throughout the processing to cover the patient sample is easier.

Example 2. A Conventional Manual PAP Smear Slide with Integrated Process Quality Controls Manual Pap smear slides are routinely made throughout the world. There is no preprocessing of the patient sample, so the smear includes mucus and other cellular debris. As detailed in WO2018/228576 by the same inventors (which is hereby incorporated by reference), incorporating known behavior chemical targets to capture the performance of the stain reagents is possible. To that end, several additional PQC targets will be applied to the blank adhesive coated slide at time of the slide's manufacture. The PQC targets can be digitally imaged and the results used to direct the usable lifetime of the stain reagents.

Example 3. A ThinPrep PAP Smear Slide with Integrated Process Quality Controls The dominant automated cervical smear processing system is the ThinPrep. The automated system takes a portion of a patient sample from a vial to filter out the mucus and to some degree any red blood cells or other debris. The cleaned sample is deposited onto an adhesive coated slide through a contact print method. The slide has four fiducial points located at roughly the four corners of a rectangle that is outside of the sample deposit area. The unique shape of the fiducial marks identifies the slide's origin, with sample processing performed by a Cytyc sample prep system, when digitally imaging the stained result. The missing element in the ThinPrep technology is on-slide Process QC to validate the staining reagents and processing are performing as needed. The PQC provides information to the imaging system of processing defects and reagent degradation that is otherwise not available. The standard Pap staining reagents, a 5-stain 3-step sequence, includes three reagents that have known drift and degradation behaviors: Hematoxylin, Eosin, and Phosphotungstic Acid. Incorporating known behavior chemical targets to capture the performance of the stain reagents is possible. To that end, several additional PQC targets will be applied to the ThinPrep slide at time of the slide's manufacture. The imaging system now has the necessary PQC information to provide feedback of the stain reagent performance and establish a foundation by which the stain color can be shifted to present a normalized view, without impacting the diagnostic decision criteria.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

The invention claimed is:

1. A slide comprising:
    a detection area configured to hold a sample comprising loose cells, wherein the detection area comprises at least one region, and
    a control area around the at least one region, wherein the control area comprises at least one control target, and the control area is configured to:
        indicate an error and performance measure of intermediate steps during an immunohistochemical or cytochemical detection process, and provide a reference for qualitatively or quantitatively determining the antigen density and color density of the stained loose cells or color density on and within the stained cells respectively.

2. The slide according to claim 1, wherein the at least one region of the detection area is bounded by a hydrophobic barrier to form a well.

3. The slide according to claim 2, wherein the well of the detection area is a round, or a square or a rectangle.

4. The slide according to claim 2, wherein the control area is at a corner of the at least one region of the detection area.

5. The slide according to claim 2, wherein the control area is inside the well of the detection area.

6. The slide of claim 1, further comprises an adhesive coating configured to bind with moieties, wherein the adhesive coating comprises at least one end group selected from the group consisting of —ROH, —R(C=O)OH, —RNH$_2$, —R(C=O)NH$_2$, and —RNH$_3$.

7. The slide according to claim 1, wherein the control area is outside the region of the detection area.

8. The slide according to claim 1, wherein the control area comprises at least one control dot or a control strip.

9. The slide according to claim 1, wherein the control area is bounded by a partial or complete hydrophobic barrier.

10. The slide according to claim 1, wherein the at least one well of the detection area comprises the sample.

11. The slide according to claim 1, further comprising a hydrophobic material coating, wherein the hydrophobic material is epoxy or urethane.

12. The slide according to claim 1, wherein the at least one control target comprises a primary target, a primary antibody, a secondary target, a secondary antibody, an imaging reference, a 2D imaging reference target, a 3D imaging reference target, or a target array.

13. The slide according to claim 1, wherein the at least one control target is configured to capture mouse, rabbit, or mouse+rabbit hosted primary antibody; mouse, rabbit, or mouse+rabbit secondary antibody; or hematoxylin and eosin stains.

14. The slide according to claim 13, wherein the primary antibody is captured at a FcyRI site by either Protein A, Protein G, Protein A/G, or a FcyRI binding peptide attached to a carrier protein or activated bead.

15. The slide according to claim 13, wherein the hematoxylin and eosin are captured by a chemical target attached to an activated bead.

16. The slide according to claim 13, wherein a pair of the primary antibody comprises two different concentrations, a first concentration at 100% and a second concentration between 30 and 70%.

17. A method of using the slide according to claim 1 for detecting cells, the method comprising:
    placing the sample comprising loose cells in the detection area, placing the at least one control target in the control area, staining the loose cells and the at least one control target, wherein the staining process comprises:
        applying at least one primary target to the control area of the slide,
        applying at least one primary target conjugated with the moiety to the control area of the slide, or applying at least one secondary target conjugated with a moiety to the control area of the slide, and
        applying a stain reagent producing color to the detection area and the control area, assessing a quality of the staining process, wherein the assessing process comprises assessing the staining result of the loose cells and the control target, and qualitative determining the status of the loose cells.

18. The method according to claim 17, wherein the at least one control target is configured to capture mouse, rabbit, or mouse+rabbit hosted primary antibody; mouse, rabbit, or mouse+rabbit secondary antibody; or hematoxylin and eosin stains.

19. The method according to claim 18, wherein the primary antibody is captured at a FcyRI site by either Protein A, Protein G, Protein A/G, or a FcyRI binding peptide attached to a carrier protein or activated bead.

20. The method according to claim 18, wherein the hematoxylin and eosin are captured by a chemical target attached to an activated bead.

\* \* \* \* \*